United States Patent
Hong et al.

(10) Patent No.: US 9,561,130 B2
(45) Date of Patent: Feb. 7, 2017

(54) NASOLACRIMAL PLUGS

(71) Applicants: Chaoyang Hong, Hangzhou (CN); Chenglong Wu, Hangzhou (CN); Xufeng Lin, Hangzhou (CN)

(72) Inventors: Chaoyang Hong, Hangzhou (CN); Chenglong Wu, Hangzhou (CN); Xufeng Lin, Hangzhou (CN)

(73) Assignee: HANGZHOU LIUCHA PHARMACEUTICAL LTD., Hangzhou (CN)

( * ) Notice: Subject to any disclaimer, the term of this patent is extended or adjusted under 35 U.S.C. 154(b) by 630 days.

(21) Appl. No.: 13/908,378

(22) Filed: Jun. 3, 2013

(65) Prior Publication Data
US 2013/0324908 A1 Dec. 5, 2013

(30) Foreign Application Priority Data
Jun. 5, 2012 (CN) .......................... 2012 1 0182127

(51) Int. Cl.
*A61F 9/007* (2006.01)
(52) U.S. Cl.
CPC ................................. *A61F 9/00772* (2013.01)
(58) Field of Classification Search
CPC ................................................... A61F 9/00772
See application file for complete search history.

(56) References Cited

U.S. PATENT DOCUMENTS

| | | | | | |
|---|---|---|---|---|---|
| 5,163,959 | A | * | 11/1992 | Herrick | A61B 17/12022 128/887 |
| 5,723,005 | A | * | 3/1998 | Herrick | A61F 9/00772 604/8 |
| 5,741,292 | A | * | 4/1998 | Mendius | A61B 17/0057 128/831 |
| 6,254,562 | B1 | * | 7/2001 | Fouere | A61F 9/00772 128/887 |
| 6,306,114 | B1 | * | 10/2001 | Freeman | A61F 9/00772 128/887 |

* cited by examiner

*Primary Examiner* — Leslie Deak
*Assistant Examiner* — Kai Weng
(74) *Attorney, Agent, or Firm* — Anova Law Group, PLLC

(57) ABSTRACT

A plug for use in a passage or conduit of a human body is provided. The plug includes a plug body with a first end and a second end. The plug body has a protrusion on an exterior wall. The plug also includes an attaching member at the first end to attach the plug to the passage or conduit. The plug further includes an axial retention tube within the plug body. The plug further includes a reservoir. The reservoir connects to the retention tube at a third end thereof. The reservoir and the retention tube are configured to regulate the flow of fluid in the passage or conduit.

18 Claims, 4 Drawing Sheets

NASOLACRIMAL PLUGS

CROSS-REFERENCES TO RELATED APPLICATIONS

This application claims the priority of Chinese patent application number 201210182127.0, filed on Jun. 5, 2012, the entire contents of which are incorporated herein by reference.

FIELD OF INVENTION

This invention relates generally to medical devices, and, more particularly, to medical devices for regulating fluid in a body part.

BACKGROUND

Keratoconjunctivitis sicca is an eye disease caused by eye dryness, which, in turn, is caused by inadequate quantity of tears or lower quality of tears in eyes. Severe eye dryness may cause pathologic changes to corneal epithelium. Usually, one eye of a person secret about 1 microliter (μl) of tears in one minute (1 μl/min). Decreased tear production or increased tear film evaporation may cause inadequate quantity of tears in eyes. As to the quality of the tears, tears with normal quality usually form a tear film over the eye surface. The tear film has three layers from outside to inside: oil layer, water layer, and mucous layer. Abnormality in any layer may cause the decrease in the quality of the tears.

Keratoconjunctivitis sicca is colloquially called dry eyes syndrome (DES). DES is usually characterized by abnormality in the quantity of tears, quality of tears, or kinetics of tears. The tear film becomes less stable. A patient may feel uncomfortable in eyes and/or have characteristic lesion on the external tissue of eyes. DES refers to a variety of diseases.

The common syndrome may include dry eyes, tiredness of eyes, sleepiness, itching eyes, sensation of foreign objectives in eyes, sensation of pain and burning in eyes, tight eyelids, thick eye secret, sensitivity to wind of eyes, sensitivity to light of eyes, sensitivity to external stimuli of eyes, and/or temporary blurring eyesight. If the eyes are too dry, the inadequacy of basal tears may stimulate the secretion of reflex tears. A patient may exhibit the symptom of tearing. A patient with severe DES may exhibit the syndrome of inflammation, hyperaemia, cornification, damages to corneal epithelium accompanied by adherence of filament material to the eyes. The chronic damages may cause pathologic changes of the cornea and conjunctiva and may affect eyesight.

For patients with keratitis at the palpebral fissure, the tear film may break in shortened time period, which may in turn cause keratitis filamentosa and/or keratoconjunctivitis sicca. The symptom may include reduction of the tear production at the palpebral fissure. Schirmer test may show the decreased tear production in patient. This disease usually appears to be an idiopathic disease among old people. The disease may also be commonly seen in patients with Sjogren's syndrome as a symptom expressed in eyes. Sjogren's syndrome may include dry mouth, dry eyes, and arthritis. The disease may also be commonly seen in patients with autoimmune diseases, and systematic diseases, such as sarcoma, and Waldenström's macroglobulinemia. The treatment methods may include artificial tears. Patients with severe symptoms may wear protective goggle or have the lacrimal puncta blocked.

For patients with the above mentioned symptoms, a physician may need to inquire the medical history to identify the cause. For patients with severe dry eye, a treating physician may need to inquire about other possible accompanying symptoms, such as dry mouth, or arthritis symptoms.

The DES symptoms may vary significantly among individual patient. Many patients complain about the sensation of foreign object in eyes, burning sensation or common uncomfortable feeling in eyes. These symptoms may be typically described as sensation of abrasion, dry eyes, pain, sensation of sand in the eyes, tingling sensation, or burning sensation. These discomforts are usually symptoms of DES, due to the fact that the surface of cornea is rich in sensory nerve endings. A significant portion of patients may be sensitive to light and have intermittent blurring eyesight or other eyesight problems. Clinically, DES constitutes a significant portion of eye disease.

Patients with DES often complain the tiredness of eyes, which cause difficulty reading and watching TV. The reason for these difficulties is that the frequency of winking is reduced when a patient concentrate on certain tasks. Normally, a person wink once for about every five (5) seconds. When the frequency of winking is reduced, the evaporation time of tear film is significantly extended. With inadequate winking, the cornea may be exposed for more than ten (10) seconds. One or more dry points may form on the surface of cornea. This occurs with relatively high ratio among young people. The average age of DES patients is reduced due to long time internet surfing, long time reading using mobile devices, and long term contact lens use among young generation.

Many DES patients may have both the decreased tear production and increased tear film evaporation. Before a treatment, a physician usually should identify the cause and take corresponding measures. DES is a chronic disease. Many patients need long term care. A physician may need to encourage a patient for long term treatment. Currently, lacrimal plug implantation has the advantage for providing long term adjuvant therapy. The plug may be removed by washing with normal saline solution. But the plug does not have regulating function. Patients with severe and mild symptom use the same type of plug. For some patient, tears may overflow and inflammation may follow. Other treatment includes closure of the lacrimal punctum using laser, which is a type of irreversible surgery.

Another treatment is fluid replacement therapy. The replacement therapy may include artificial tear replacement therapy and hormonal eyedrops. The artificial tear replacement therapy requires long term or even life time administration of the medicine. Further, the artificial tear and the additive therein may exacerbate the symptom. When a patient uses hormonal eyedrops, there is a risk that it would induce severe complication. The side effect is obvious.

The disclosed nasolacrimal plugs are directed at solving one or more problems set forth above and other problems.

BRIEF SUMMARY OF THE DISCLOSURE

One aspect of the present disclosure provides a plug for use in a passage or conduit of a human body. The plug includes a plug body with a first end and a second end. The plug body has a protrusion on an exterior wall. The plug also includes an attaching member at the first end to attach the plug to the passage or conduit. The plug further includes an axial retention tube within the plug body. The plug further includes a reservoir. The reservoir connects to the retention tube at a third end thereof. The reservoir and the retention tube are configured to regulate the flow of fluid in the passage or conduit.

Another aspect of the present disclosure provides a plug implantation tool for implanting the plug according to this disclosure. The implantation tool includes a shell body with a first end and a second end. The implantation tool also includes a sleeve with an outside end at the first end of the shell body. The implantation tool includes a first shaft with a linking end. The first shaft is configured to slide within the sleeve and to be reversibly inserted in the retention tube of the plug. The implantation tool further includes a sliding button and a linking member. The linking member connects the linking end and the sliding button.

Another aspect of the present disclosure provides a plug for use in a passage or conduit of a human body. The plug includes an attaching member with an opening. The attaching member is configured to attach the plug to the passage or conduit. The plug also includes a reservoir with an elastic wall. The reservoir is configured to receive fluid from the opening. The wall is configured to be deformed reversibly when receiving pressure and to maintain the position of the plug in the passage or conduit. The plug further includes a retention tube. The retention tube is configured to receive fluid from the reservoir. The reservoir and the retention tube are configured to regulate the flow of fluid in the passage or conduit.

Another aspect of the present disclosure provides a plug for use in a passage or conduit of a human body. The plug includes an attaching member, which is configured to attach the plug to the passage or conduit. The plug also includes a first body and a second body. The second body has a thickened wall to form a bulge. The bulge is configured to press against the wall of the passage or conduit to facilitate the maintenance of the position of the plug in the passage or conduit. The plug further includes a first tube within the plug and a second tube within the plug. The first tube and the second tube are configured to regulate the flow of fluid in the passage or conduit.

Other aspects of the present disclosure can be understood by those skilled in the art in light of the description, the claims, and the drawings of the present disclosure.

DETAILED DESCRIPTION

Reference will now be made in detail to exemplary embodiments of the invention, which are illustrated in the accompanying drawings. Wherever possible, the same reference numbers will be used throughout the drawings to refer to the same or like parts.

Figure 1:
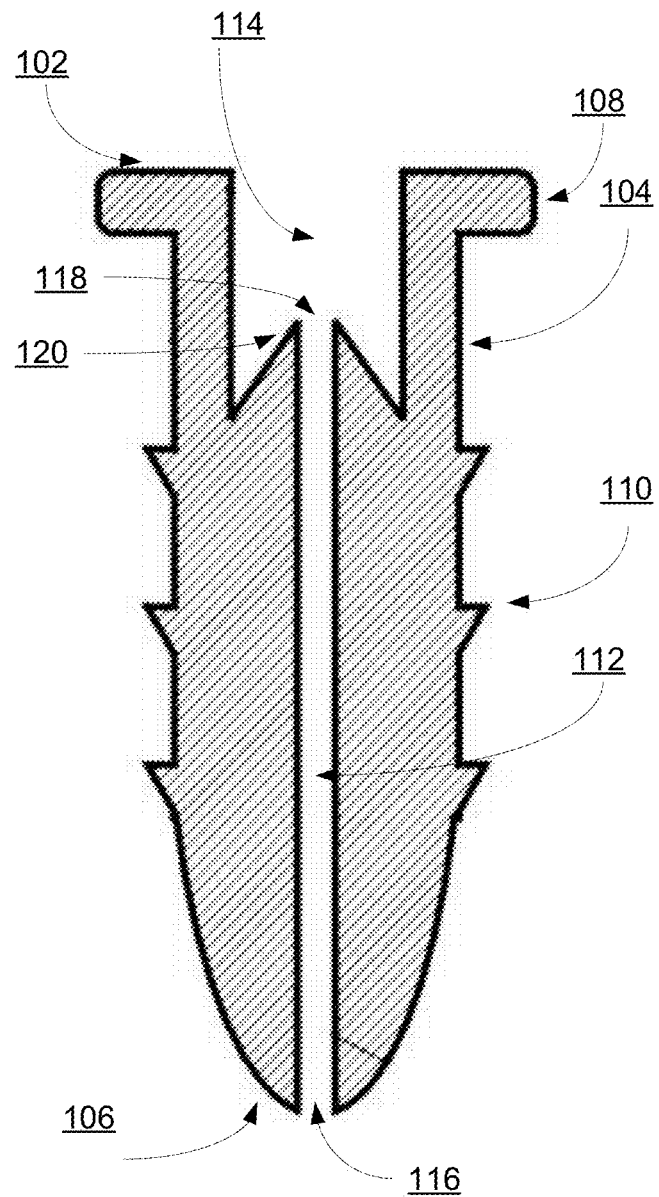
FIG. 1 illustrates an exemplary nasolacrimal plug consistent with the disclosed embodiments.

FIG. 1 illustrates a longitudinal section view of an exemplary plug 100 consistent with the disclosed embodiments. As shown in FIG. 1, the plug 100 includes a first end 102, a body 104, a second end 106, an attaching member 108, a protrusion 110, a capillary retention tube 112, and a reservoir 114.

The transverse section of the body 104 may be in an appropriate shape. In certain embodiments, the transverse section of the body 104 may be in a substantially circular shape. The transverse section of the attaching member 108 may or may not be in the same shape as the body 104. The size of the cross section of the body 104 is configured to allow the plug 100 to be placed in the nasolacrimal duct. In certain embodiments where the transverse section of the body 104 is substantially circular, the diameter of the transverse section of the body 104 may be ranged from 0.5 millimeter (mm) to 1.2 mm. The area of the transverse section of the body 104 may vary. The shape and the area of the transverse section of the body 104 may be determined empirically. The length of the body 104 may be configured to allow the plug 100 to be implanted in the nasolacrimal duct of a patient.

The attaching member 108 is located at the first end 102. The attaching member 108 is configured to attach the plug 100 to the nasolacrimal duct. The attaching member 108 may attach to the lacrimal puctum and prevent the plug 100 from entering the nasolacrimal duct completely. That is, while the body 104 may enter the nasolacrimal duct, the first end 102 remains outside of the nasolacrimal duct. In certain embodiments, the attaching member 108 is a flange plate.

The transverse section of the attaching member 108 may have a greater area than that of the body 104. In certain embodiments where the transverse section of the attaching member 108 is substantially circular, the diameter of the transverse section of the member 108 may be ranged from 0.6 mm to 2 mm. The transverse section of the attaching member 108 may be in other appropriate shape and may have other appropriate area value. The shape and/or size of the transverse section of the attaching member 108 may be determined empirically.

The plug 100 may include the protrusion 110 on the exterior wall of the body 104. In certain embodiments, the plug 100 may include more than one protrusion 110, such as two or three protrusions 110. The plug 100 may also have other numbers of protrusions 110. The transverse section of the protrusion 110 may be in an appropriate shape. The transverse section of the protrusion 110 may or may not be in the same shape as the body 104. The protrusion 110 is configured to prevent the plug 100 from sliding freely once the plug 100 is implanted in the nasolacrimal duct. The protrusion 110 is also configured to allow the removal of the plug 100 from the nasolacrimal duct if desired.

In certain embodiments where the transverse section of the protrusion 110 is substantially circular, the diameter of the transverse section of the protrusion 110 may be ranged from 0.6 mm to 2 mm. The protrusion 110 may have other transverse section dimension. In certain embodiments, the distance between two adjacent protrusions 110 may be about 0.1 mm. The distance between two adjacent protrusions 110 may vary based on empirical data.

The plug 100 includes the second end 106. In certain embodiments, the second end 106 may be taper round end.

The plug 100 includes the capillary retention tube 112. The tube 112 may be located in an appropriate position within the body 104. In certain embodiments, the tube 112 is located at the center of the body 104. The tube 112 may be in an appropriate shape. In certain embodiments, the transverse section of the tube 112 is substantially circular. The area of the transverse section of the tube 112 may be uniform along the tube or may vary along the tube. The area of the transverse section of the tube 112 is configured for the plug to regulate the tears within the eyes. The area of the transverse section of the tube 112 is large enough to allow the tears to enter the tube 112 and to allow the tears to flow within the tube 112. On the other hand, the area of the transverse section of the tube 112 is small enough to prevent the direct loss of the tears. That is, the tube 112 is configured to retain tears until certain condition is met. In certain embodiments where the transverse section of the tube 112 is substantially circular, the diameter of the transverse section of the tube 112 may be ranged from 0.1 mm to 0.6 mm. The area of the transverse section of the tube 112 may have other value.

The tube 112 includes two openings. A first opening 116 is located at the second end 106 of the plug 100. A second opening 118 is located at a third end 120, where the tube 112 is connected to the reservoir 114. The third end 120 may be in a conical convex shape.

The plug 100 includes the reservoir 114. The reservoir 114 is configured to hold certain amount of tears. Tears may enter the reservoir 114. When the amount of tears in the reservoir 114 is small, the tube 112 siphons the tears into the tube 112 by capillary force. The tears in the tube 112 are retained and function as a blocker to keep the tears within the eyes by the capillary force of the tube 112. The tears in the eyes may exceed certain quantity and enter an overflow state. In overflow state, the tears in the reservoir 114 reach certain amount and create a pressure. The pressure may push the tears in the tube 112 flow through the nasolacrimal duct into the nasal cavity. The amount of tears needed to create the pressure and the volume of the reservoir 114 may be determined empirically.

The plug 100 may be made of materials that are appropriate for implantation in the nasolacrimal duct. The appropriate materials includes, but not limited to, titanium, medical stainless steel, nitinol, silicone, medical silica gel, polyethylene, or chitin. Other appropriate materials may also be used.

Figure 2:
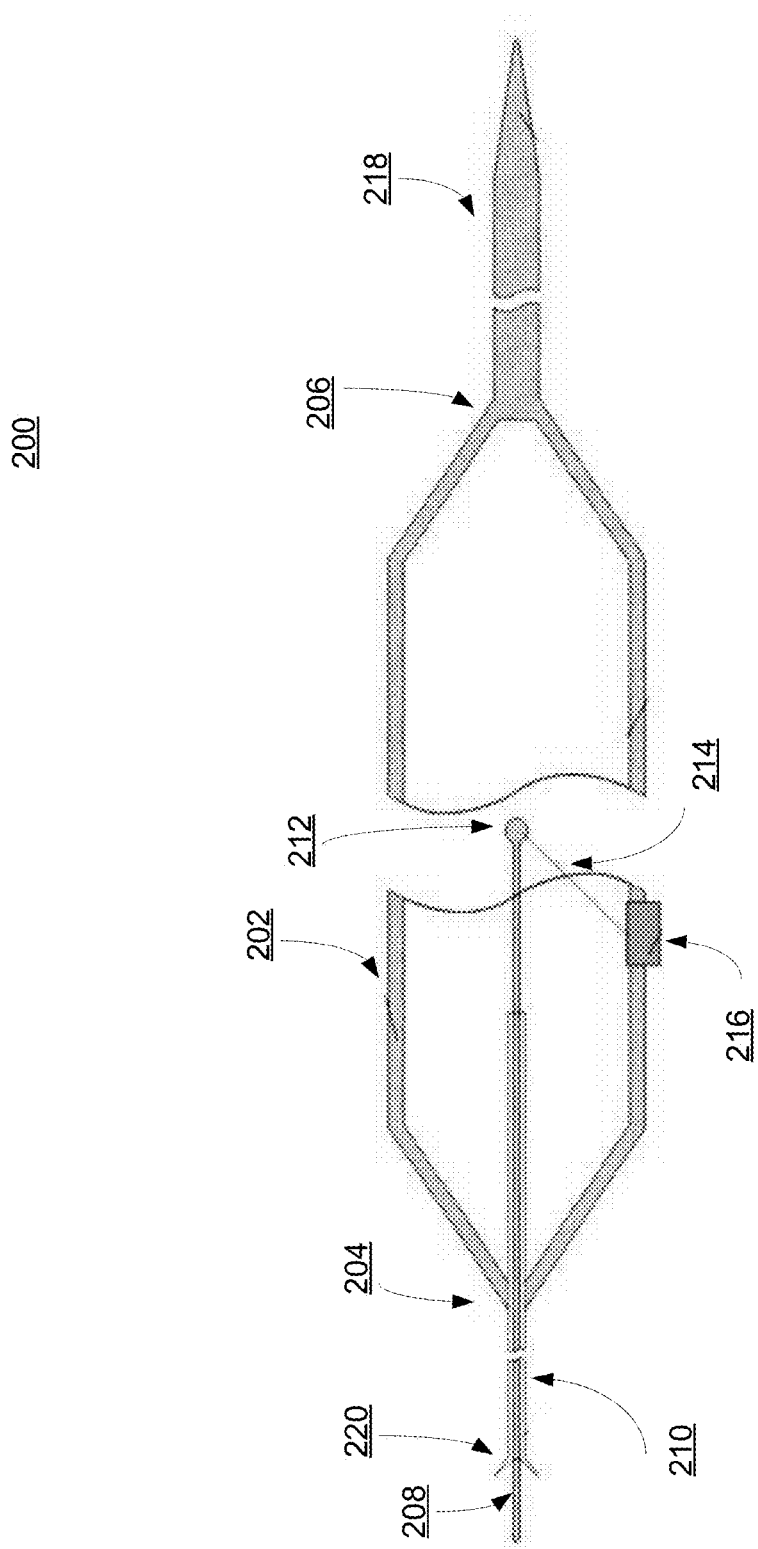
FIG. 2 illustrates an exemplary nasolacrimal plug implantation tool consistent with the disclosed embodiments.

FIG. 2 illustrates an exemplary plug implantation tool 200 consistent with the disclosed embodiments. As shown in FIG. 2, the tool 200 may include a shell body 202, a first end 204, a second end 206, a first shaft 208, a sleeve 210, linking member 214, a sliding member 216, and a second shaft 218.

The first shaft 208 may be a needle-like shaft. That is, the first shaft 208 may have a transverse section with small area. The area of the transverse section of the first shaft 208 may be determined empirically. The transverse section of the first shaft 208 may be in an appropriate shape. In certain embodiments, the first shaft 208 is configured to be placed in the tube 112 of the plug 100. Thus, the first shaft 208 may be used as a guide to implant the plug 100 into the nasolacrimal duct. The length of the first shaft 208 may be configured to allow the first shaft 208 to deliver the plug 100 into the nasolacrimal duct.

The first shaft 208 has a linking end 212 located within the shell body 202. The linking end 212 may be attached to the linking member 214, which in turn is attached to the sliding member 216. The sliding member 216 may be located on a sliding mechanism which allows the sliding member 216 to move axially along the shell body 202.

The shell body 202 is configured to accommodate the shaft 208 and the sleeve 210. The shell body 202 is also configured to allow a user to handle the implantation tool 200. In certain embodiments, the shell body 202 has a transverse section in substantially circular shape. The diameter of the transverse section may be ranged from about 10 mm to 30 mm. The transverse section of the shell body 202 may have other appropriate shape. The area of the transverse section of the shell body 202 may be adjusted empirically.

The second shaft 218 may be configured to prepare the nasolacrimal duct for implantation. More particularly, the second shaft 218 may be configured to clean and/or dilate the nasolacrimal duct of a patient. The transverse section of the second shaft 218 may be in an appropriate shape and may have a size that is appropriate for cleaning and/or dilating the nasolacrimal duct. In certain embodiments, the transverse section of the second shaft 218 is substantially circular. The diameter of the second shaft 218 at the tip end may be about 0.1 mm.

The first shaft 208 may be placed in the sleeve 210. The sleeve 210 may be configured to have a shorter length than that of the first shaft 208. The sleeve 210 may also be configured to allow the first shaft 208 to slide therein. The sleeve 210 has an outer end 220, which may be configured to have a shape complementarily matching the shape of the third end 120. The outer end 220 and the third end 120 may be temporarily attached to allow the first shaft 208 to guide the plug 100. In certain embodiments, the outer end 220 may have a conical concave shape.

The implantation tool 200 may be used to implant the plug 100 in the nasolacrimal duct of a patient. The second shaft 218 may be used to prepare the nasolacrimal duct of a patient for implantation. Particularly, the second shaft 218 may clean and dilate the nasolacrimal duct of a patient before the implantation. The plug 100 may be placed on the shaft 208 with the shaft 208 being inserted in the tube 112. The third end 120 of the tube 112 may temporarily attach to the outer end 220. The plug 100 may be inserted into the nasolacrimal duct of a patient facilitated by the implantation tool 200. A user may slide the sliding button 216 to remove the first shaft 208 from the plug 100. The plug 100 may be then left within the nasolacrimal duct of a patient.

Figure 3:
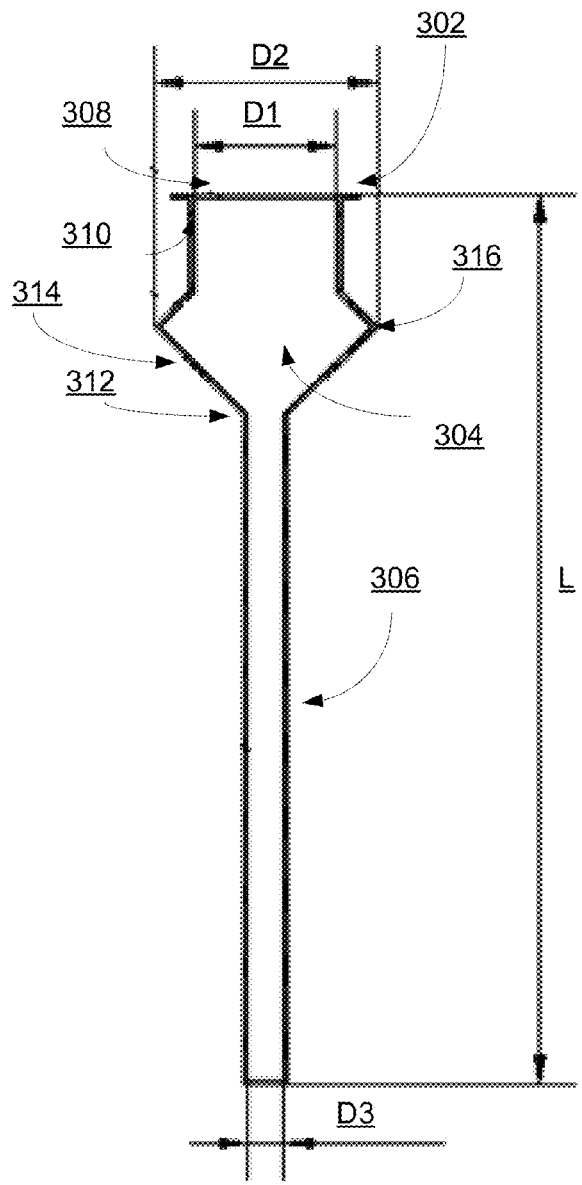
FIG. 3 illustrates an exemplary nasolacrimal plug consistent with the disclosed embodiments.

FIG. 3 illustrates an exemplary plug 300 consistent with the disclosed embodiments. As shown in FIG. 3, the plug 300 may include an attaching member 302, a reservoir 304, and a retention tube 306. The attaching member 302 may have an opening 308. The attaching member 302 is configured to attach the plug 300 to the nasolacrimal duct of a patient and may be in an appropriate shape and have an appropriate size. The attaching member 302 may attach to the lacrimal puctum and prevent the plug 300 from entering the nasolacrimal duct completely. That is, while the reservoir 302 and the retention tube 306 may enter the nasolacrimal duct, the attaching member 203 remains attached to the lacrimal punctum.

The opening 308 is configured to allow the tears in the eye of a patient to enter the reservoir 304 and may be in an appropriate shape and have an appropriate size. In certain embodiments, the transverse section of the opening 308 may be substantially circular. The opening 308 may have a diameter D1 at about 0.8 mm. The shape and the size of the opening 308 may be adjusted and determined empirically. The opening 308 may be located in an appropriate position on the attaching member 302. In certain embodiments, the opening 308 is located at the center of the attaching member 302.

The reservoir 304 may have a first end 310 and a second end 312. The reservoir 304 has an elastic wall 314, which may be made of an elastic material. The elastic wall 314 may be reversibly deformed under pressure. The transverse section of the reservoir 304 may be in an appropriate shape and have an appropriate size. The elastic wall 314 may have a bulge 316, where the area of the transverse section of the reservoir 304 is enlarged. In certain embodiments where the transverse section of the reservoir is substantially circular, the diameter D2 of the bulge 316 may be about 1.2 mm when the plug 300 does not receive a pressure on the wall 314 and the elastic material forming the wall is in a relax state. The shape and size of the bulge 316 may be adjusted and determined empirically.

A user may implant the plug 300 in the nasolacrimal duct of a patient. During the implantation, the bulge 316 is pressed and deformed to facilitate the implantation of the plug 300. After the plug 300 is inserted in the nasolacrimal duct, the elastic force of the wall 314 causes the bulge to enlarge again. The enlarged bulge 314 may press against the wall of the nasolacrimal duct and prevent the free movement of the plug 300 in the nasolacrimal duct.

The reservoir 304 may be located at an appropriate location along the longitudinal axis of the plug 300. In certain embodiments, the reservoir 304 is located close to the attaching member 302 with the first end 310 attached to the attaching member 302 and the second end 312 connected to the retention tube 306. The plug 300 may have one or more reservoir 304.

The plug 300 may include the retention tube 306. The tube 306 is configured to be suitable for implantation in the nasolacrimal duct of a patient. The tube 306 may be in an appropriate shape. In certain embodiments, the transverse section of the tube 306 is substantially circular. The area of the transverse section of the tube 306 may or may not be uniform along the tube or may vary along the tube. The area of the transverse section of the tube 306 is configured for the plug to regulate the tears within the eyes. The area of the transverse section of the tube 306 is large enough to allow the tears to enter the tube 306 and to allow the tears to flow within the tube 306. On the other hand, the area of the transverse section of the tube 306 is small enough to prevent the direct loss of the tears. That is, the tube 306 is configured to retain tears by capillary force until certain condition is met. In certain embodiments where the transverse section of the tube 306 is substantially circular, the diameter D3 of the transverse section of the tube 306 may be about 0.2 mm. The shape and size of the transverse section of the tube 306 may be adjusted and determined empirically.

After the plug 300 is implanted in the nasolacrimal duct of a patient, tears may enter the reservoir 304 through the opening 308. When the amount of tears in the reservoir 304 is small, the tube 306 siphons the tears into the tube 306 by capillary force. The tears in the tube 306 are retained and function as a blocker to keep the tears within the eyes. The tears in the eyes may exceed certain quantity and enter an overflow state. In overflow state, the tears in the reservoir 304 reach a threshold amount and create a pressure. The pressure may push the tears in the tube 306 flow through the nasolacrimal duct into the nasal cavity. The threshold amount to create the pressure and the volume of the reservoir 304 may be determined empirically.

The plug 300 has a length L, which may be configured for the implantation in the nasolacrimal duct. In certain embodiments, the length L may be about 5 mm when the plug 300 is not receiving a pressure on the wall 314. In other words, when the bulge 316 is not pressed to be deformed, and the wall 314 is in a relax state, the length L may be about 5 mm. The length L of the plug 300 may be adjusted and determined empirically.

Figure 4:
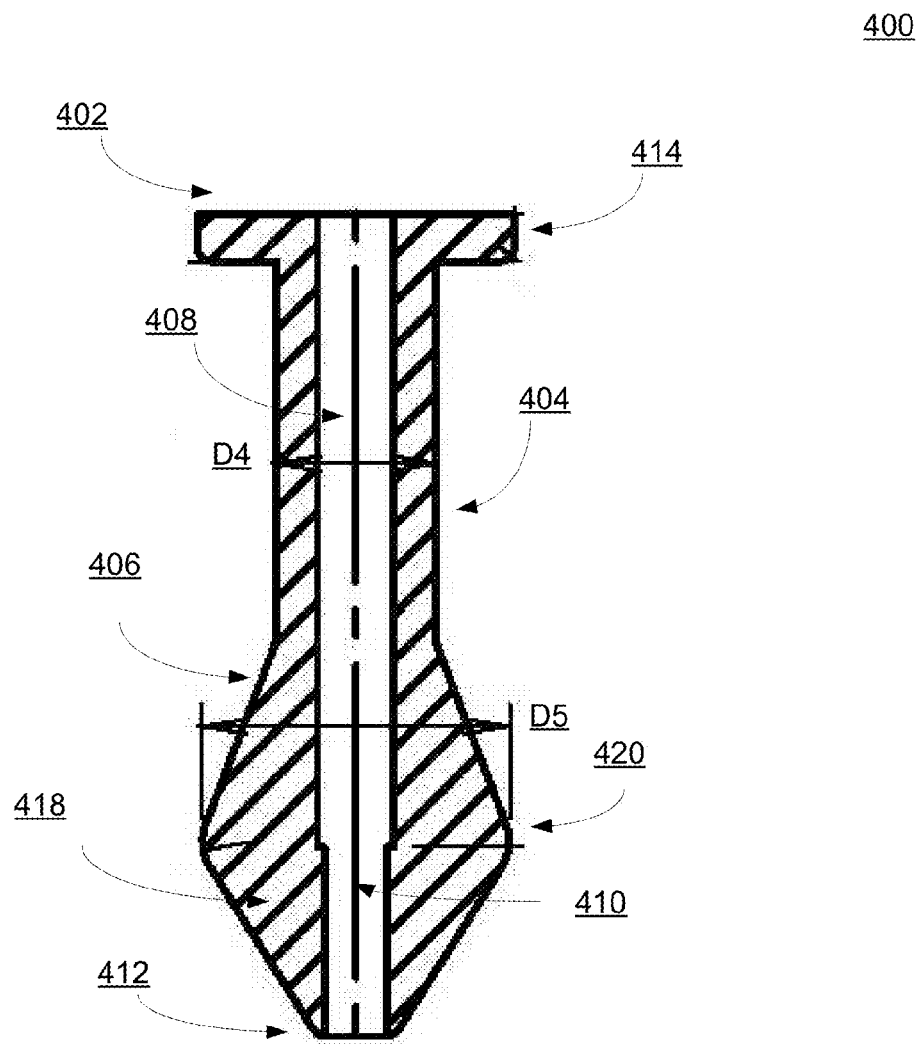
FIG. 4 illustrates an exemplary nasolacrimal plug consistent with the disclosed embodiments.

FIG. 4 illustrates an exemplary plug 400 consistent with the disclosed embodiments. As shown in FIG. 4, the plug 400 includes a first end 402, an attaching member 414, a first body 404, a second body 406, a first tube 408, a second tube 410, and a second end 412.

An attaching member 414 may be located at the first end 402. The attaching member 414 is configured to attach the plug 400 to the nasolacrimal duct of a patient. The attaching member 414 may attach to the lacrimal puctum and prevent the plug 400 from entering the nasolacrimal duct completely. That is, while the other parts of the plug 400 may enter the nasolacrimal duct, the first end 402 remains outside of the nasolacrimal duct. In certain embodiments, the attaching member 414 is a flange plate. The transverse section of the attaching member 414 may be in an appropriate shape and have an appropriate size. The transverse section of the attaching member 414 may have a larger area than that of the first body 404. In certain embodiments, the transverse section of the attaching member 414 may be substantially circular and the diameter may be about 1 mm. The shape and the size of the transverse section of the attaching member 414 may be adjusted and determined empirically.

As shown in FIG. 4, the first body 404 is attached to the attaching member 414 at one end, and to the second body 406 at another end. The first body 404 is configured for the use of the plug 400 in nasolacrimal duct. The transverse section of the first body 404 may be in an appropriate shape and have an appropriate size. In certain embodiment, the transverse section of the first body 404 may be substantially circular and the diameter D4 may be about 0.5 mm to 0.6 mm. The size and shape of the transverse section of the first body 404 may be adjusted and determined empirically. The transverse section of the first body 404 may be or may not be uniform in size and/or shape along the longitudinal axis of the body 404.

As shown in FIG. 4, the wall 418 of the second body 406 may be thickened. As a result, a bulge 420 may be formed on the second body 406. The second body 406 is configured to allow the implantation and relatively stable positioning of the plug 400 in the nasolacrimal duct. That is, after the plug 400 is implanted, the plug 400 may not move freely. Therefore, the bulge 420 may be configured to exert pressure to the wall of the nasolacrimal duct and as a result, the plug 400 is maintained in a relatively stable position. The wall 418 may be made of an appropriate elastic material to allow the bulge 420 to exert pressure on the wall of the nasolacrimal duct. The wall 418 may also be made of other appropriate materials.

The transverse section of the second body 406 may be in an appropriate shape and have an appropriate size. In certain embodiments, the transverse section of the second body 406 is substantially circular and has a maximum diameter D5 of about 1 mm at the bulge 420. The size and shape of the transverse section of the second body 406 may be adjusted and determined empirically.

As shown in FIG. 4, the plug 400 may have the first tube 408 and the second tube 410. The transverse section of the first tube 408 and the second tube 410 may be in an appropriate shape and have an appropriate size. The transverse section of the first tube 408 may or may not be in the same shape and/or have the same size as the second tube 410. In certain embodiments, the transverse section of the first tube 408 has a greater area than that of the second tube 410. In certain embodiments, the transverse section of the first tube 408 is substantially circular and has a diameter of about 0.3 mm. The transverse section of the second tube 410 is also substantially circular and has a diameter of about 0.2 mm. Transverse section area and the length of the first tube 408 and those of the second tube 410 may be adjusted and determined empirically. The shape and/or size of the transverse section of the first tube 408 may or may not be uniform along the longitudinal axis of the first tube 408. The shape and/or size of the transverse section of the first tube 410 may or may not be uniform along the longitudinal axis of the first tube 410.

In certain embodiments, the first tube 408 may function as a reservoir. After the plug is implanted, the tears may enter the first tube 408. The second tube 410 may siphon the tears in the first tube 408 into the second tube 410 by capillary force. The tears in the second tube 410 may be retained and function as a blocker to prevent the loss of the tears from the plug 400. When the tears in the eye of a patient reach a certain level, the amount of tears in the first tube 408 exceed a predetermined threshold and create a pressure that is sufficiently great to push the tears out of the second tube 410 in to the nasal cavity. The amount of tears needed to reach the threshold may be determined empirically.

The present disclosure provides advantages. A plug consistent with the disclosed embodiments may dynamically regulate the amount of tears in eyes automatically through the siphoning of the retention tube. The plug consistent with the disclosed embodiments may prevent overflow of tears in the eyes of a patient and increase the tears in the eyes of a patient to a reasonable amount. Thus, the plug may relieve a DES patient from a variety of discomforts and improve the symptom scientifically. The plug may also effective prevent the overflow of tears in eyes of a patient which may be commonly seen in a patient with blocked nasolacrimal duct. Thus, the plug may reduce the possibility of inflammation in nasolacrimal duct of a patient because the patient is less likely to rub eyes with hands. Moreover, the nasolacrimal duct is not completely blocked. Thus, the possibility of inflammation of the nasolacrimal duct due to lack of washing by tears may also be reduced. The plug implantation tool may facilitate the implantation of the plug.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications. For example, the size, shape, appearance and the thickness of wall of the plug according to the present disclosure may be adjusted to make a plug or a stent that may be suitable for the use in other natural passage/conduit in a human body, such as prostate.

What is claimed is:

1. A plug for use in a passage or conduit of a human body, comprising:
   a plug body with a first end and a second end, the plug body having a protrusion on an exterior wall;
   an attaching member at the first end, the attaching member configured to attach the plug to the passage or conduit;
   an axial retention tube within the plug body; and
   a reservoir attached to the attaching member, wherein the reservoir connects to the retention tube at a third end thereof,
   wherein:
      the reservoir and the retention tube are configured to regulate the flow of fluid in the passage or conduit;
      the retention tube has a diameter ranging from about 0.1 millimeter (mm) to 0.6 mm;
      a diameter of a transverse section of the reservoir is greater than the diameter of the retention tube;
      the retention tube is free of obstruction; and
      the plug is configured to regulate the flow of tears in nasolacrimal duct, including: when the retention tube is empty and there is fluid in the reservoir, siphoning the fluid into the retention tube by a capillary force, wherein:
         when the fluid in the reservoir is below a threshold amount, the fluid is not drained by the retention tube; and
         when the fluid in the reservoir is above a threshold amount, the fluid is drained through the retention tube to flow through the nasolacrimal duct into the nasal cavity.

2. The plug according to claim 1, wherein:
   the retention tube has a diameter ranging from about 0.2 mm to 0.4 mm.

3. The plug according to claim 1, wherein:
   the plug body has a plurality of discrete protrusions, and a transverse section of each protrusion is substantially circular.

4. The plug according to claim 3, wherein:
   the distance between two adjacent protrusions is about 0.1 mm.

5. The plug according to claim 1, wherein:
   the plug is made of a material selected from the group consisting of titanium, medical stainless steel, nitinol, silicone, medical silica gel, polyethylene, and chitin.

6. A plug implantation tool for implanting the plug according to claim 1, comprising:
   a shell body with a first end and a second end;
   a sleeve with an outside end at the first end of the shell body;
   a first shaft with a linking end, the first shaft being configured to slide within the sleeve and be reversibly inserted in the retention tube of the plug;
   a sliding button; and
   a linking member, wherein:
      the linking member connects the linking end and the sliding button.

7. The plug implantation tool according to claim 6, wherein:
   the outside end of the sleeve complementarily matches the third end of the retention tube.

8. The plug implantation tool according to claim 6, further comprising:
   a second shaft.

9. The plug implantation tool according to claim 8, wherein:
   the second shaft is configured to prepare the passage or conduit for implantation.

10. The plug according to claim 1, wherein:
    the diameter of the transverse section of the reservoir is at least two times of the diameter of the retention tube.

11. A plug for use in a passage or conduit of a human body, comprising:
    a plug body with a first end and a second end, the plug body having a protrusion on an exterior wall;
    an attaching member at the first end, the attaching member configured to attach the plug to the passage or conduit;
    an axial retention tube within the plug body; and
    a reservoir attached to the attaching member, wherein the reservoir connects to the retention tube at a third end thereof,
    wherein:
       the reservoir and the retention tube are configured to regulate the flow of fluid in the passage or conduit;
       a diameter of a transverse section of the reservoir is greater than the diameter of the retention tube;
       the retention tube is free of obstruction;

the reservoir retains fluid in the reservoir without draining the fluid through the retention tube when the fluid is below a threshold amount; and when the fluid in the reservoir is above a threshold amount, the fluid is drained through the retention tube to flow through the nasolacrimal duct into the nasal cavity.

12. The plug according to claim 11, wherein a lower portion of the reservoir is shaped to retain the fluid in the reservoir below a level at which the reservoir connects to the retention tube.

13. The plug according to claim 12, wherein:
the plug is configured to regulate the flow of tears in nasolacrimal duct.

14. The plug according to claim 13, wherein:
the retention tube has a diameter ranging from about 0.1 millimeter (mm) to 0.6 mm.

15. The plug according to claim 14, wherein:
the retention tube has a diameter ranging from about 0.2 mm to 0.4 mm.

16. The plug according to claim 12, wherein:
the plug body has a plurality of discrete protrusions, and a transverse section of each protrusion is substantially circular.

17. The plug according to claim 16, wherein:
the distance between two adjacent protrusions is about 0.1 mm.

18. The plug according to claim 11, wherein:
the plug is made of a material selected from the group consisting of titanium, medical stainless steel, nitinol, silicone, medical silica gel, polyethylene, and chitin.

\* \* \* \* \*